United States Patent
Moffatt

(10) Patent No.: US 9,204,818 B2
(45) Date of Patent: Dec. 8, 2015

(54) DRIVE SYSTEM FOR A HEAD CLAMP FOR USE IN IMAGING BY MAGNETIC RESONANCE AND X-RAY

(71) Applicant: IMRIS INC., Winnipeg, CA (US)

(72) Inventor: Steven Moffatt, Winnipeg (CA)

(73) Assignee: Imris Inc, Winnipeg, MB (CA)

( * ) Notice: Subject to any disclaimer, the term of this patent is extended or adjusted under 35 U.S.C. 154(b) by 576 days.

(21) Appl. No.: 13/690,385

(22) Filed: Nov. 30, 2012

(65) Prior Publication Data

US 2013/0190604 A1  Jul. 25, 2013

Related U.S. Application Data

(60) Provisional application No. 61/586,944, filed on Jan. 16, 2012.

(51) Int. Cl.

| A61G 13/12 | (2006.01) |
|---|---|
| A61B 5/055 | (2006.01) |
| A61B 19/00 | (2006.01) |
| A61B 6/04 | (2006.01) |
| A61B 6/00 | (2006.01) |
| A61B 17/00 | (2006.01) |

(52) U.S. Cl.
CPC .............. *A61B 5/0555* (2013.01); *A61B 6/0421* (2013.01); *A61B 6/4417* (2013.01); *A61B 6/4441* (2013.01); *A61B 6/501* (2013.01); *A61B 19/203* (2013.01); *A61B 2017/0092* (2013.01); *A61B 2017/00911* (2013.01); *A61B 2019/464* (2013.01); *A61B 2019/4857* (2013.01)

(58) Field of Classification Search
CPC ...................................................... A61G 13/12

USPC .......................................... 5/621–622, 637, 640
See application file for complete search history.

(56) References Cited

U.S. PATENT DOCUMENTS

| 3,099,441 | A | * | 7/1963 | Ries ................................... 5/637 |
| 3,835,861 | A | * | 9/1974 | Kees et al. ......................... 5/637 |
| 4,595,899 | A | | 6/1986 | Smith |
| 5,099,846 | A | | 3/1992 | Hardy |
| 5,269,034 | A | * | 12/1993 | Day et al. ........................... 5/637 |
| 5,291,890 | A | | 3/1994 | Cline |

(Continued)

FOREIGN PATENT DOCUMENTS

| DE | 3931854 | 4/1991 |
| JP | 4183446 | 6/1992 |

(Continued)

*Primary Examiner* — Fredrick Conley
(74) *Attorney, Agent, or Firm* — Adrian D. Battison; Ade & Company Inc.

(57) ABSTRACT

A head clamp for Magnetic Resonance and X-ray imaging is generally C-shaped including a base and two legs carrying pin clamp members. A course and fine adjustment system allows one of the clamp members to move inwardly relative to the other and then to be finely adjusted so as to apply a clamping force to the skull. The C-shaped support member comprises a truss with a C-shaped inner band adjacent the skull, an outer band generally following the shape of inner band and a plurality of openings defining spaced bars between the inner band and the outer band. The adjustment system comprises a screw that adjusts the width of the C-shaped member at the base and at one leg and includes a gauge to measure force applied with the mechanism located outside the field of view of the head both vertically and horizontally.

19 Claims, 9 Drawing Sheets

(56) References Cited

U.S. PATENT DOCUMENTS

| | | | |
|---|---|---|---|
| 5,537,704 A * | 7/1996 | Dinkler | ............................ 5/622 |
| 5,713,357 A | 2/1998 | Meulenbrugge | |
| 5,735,278 A | 4/1998 | Hoult et al. | |
| 5,807,254 A | 9/1998 | Meulenbrugge et al. | |
| 5,865,780 A | 2/1999 | Tuite | |
| 6,101,239 A | 8/2000 | Kawasaki | |
| 6,385,480 B1 | 5/2002 | Bachus et al. | |
| 6,658,085 B2 | 12/2003 | Sklebitz | |
| 6,754,519 B1 | 6/2004 | Hefetz | |
| 6,812,700 B2 | 11/2004 | Fahrig | |
| 6,961,606 B2 | 11/2005 | DeSilits | |
| 6,975,895 B1 | 12/2005 | Pelc | |
| 2006/0239524 A1 | 10/2006 | Desh | |

FOREIGN PATENT DOCUMENTS

| | | |
|---|---|---|
| JP | 05344964 | 12/1993 |
| WO | 2007147233 | 12/2007 |
| WO | 2010111772 | 10/2010 |

* cited by examiner

DRIVE SYSTEM FOR A HEAD CLAMP FOR USE IN IMAGING BY MAGNETIC RESONANCE AND X-RAY

This application claims the benefit under 35 USC 119(e) of Provisional Application 61/586,944 filed Jan. 16, 2012.

This invention relates to a head clamp for use in imaging by magnetic resonance (MRI) and X-Ray of a patient.

BACKGROUND OF THE INVENTION

With MRI, a high field magnet, typically superconducting, is arranged in a torus configuration (like a donut) and with the patient lying down inside the magnet on a table where the magnetic field allows a pulsed and sequenced magnetic and EM field to probe the body to produce images, which allow the trained radiologist to determine with high probability the anatomy of the patient. MRI is sometimes performed using contrast agents introduced to the patient to provide even better contrast between different tissue types. MRI techniques are very good at detecting the anatomical location of different diseases, for example, tumours.

In U.S. Pat. No. 5,735,278 (Hoult et al) issued Apr. 7, 1998, disclosed a medical procedure where a magnet is movable relative to a patient and relative to other components of the system. The moving magnet system allows intra-operative MRI imaging to occur more easily in neurosurgery patients, and has additional applications for liver, breast, spine and cardiac surgery patients.

In Published PCT Application WO07147233A1 of the present Applicants published Dec. 27, 2007 and entitled ROTATABLE INTEGRATED SCANNER FOR DIAGNOSTIC AND SURGICAL IMAGING APPLICATIONS is disclosed an improvement to the above patent in which an additional rotational movement of the magnet is allowed.

A scanning system is known in which the patient is moved from an X-ray imaging system to an MR imaging system by transferring the patient from one imaging system to the other, for example, on a moveable table. The MR scanner is used to provide information complementary to that obtained using X-ray. It can be used, for example, to perform a baseline assessment prior to intervention as well as to perform a post-intervention assessment. Such an assessment may include perfusion and viability studies of the heart or of the brain.

U.S. Pat. No. 5,713,357 (Meulenbrugge) issued Feb. 3, 1998 and related U.S. Pat. No. 5,807,254 both of Phillips shows a combination of an X-ray system and an MRI system. The system is not for intra-operative uses and the magnet is not a cylinder. The magnet is not moved. The X-ray is moved side to side in FIG. 2. The patient is moved in FIG. 1.

U.S. Pat. No. 6,101,239 (Kawasaki) issued Aug. 8, 2000 to Hitachi provides an X ray and MRI operating simultaneously at the same location and methods to operate them in a timed manner to avoid interference. However this arrangement is not suitable for interventions by the medical team since the presence of the machines restricts access to the patient.

U.S. Pat. No. 6,385,480 (Bachus) issued May 7, 2002 of Siemens discloses what they call an angio-MR system where the radiographic angio-system cooperates with the MR system. There is provided a moving patient table which transfers the patient from the X-ray system at one location to the MRI at a second location.

US Patent Application 2006/0239524 (Desh) published Oct. 26, 2006 of Siemens relates to diagnosis and treatment of cardiac diseases using MRI and X-ray. This is directed to a method of combining the images to analyze the diagnosis.

U.S. Pat. No. 6,975,895 (Pelc) issued Dec. 13, 2005 to Leland Stanford University provides a modified X ray tube for use in magnetic fields of an MRI system.

U.S. Pat. No. 6,812,700 (Fahrig) issued Nov. 2, 2004 of Leland Stanford University discloses a related system in which the perturbations in the magnetic field of the MRI caused by the X-ray system are compensated.

U.S. Pat. No. 6,658,085 (Sklebitz) issued Dec. 2, 2003 of Siemens discloses a system in which current for the coils generating the magnetic field of the MRI is calculated to reduce stray fields in the area of the X-ray system.

U.S. Pat. No. 5,865,780 (Tuite) issued Feb. 2, 1999 of SDGI Holdings discloses a device for engaging and holding the body of the patient during procedures in MRI and X-ray imaging.

U.S. Pat. No. 4,595,899 (Smith) issued Jun. 17, 1986 to Leland Stanford University provides an MRI system.

U.S. Pat. No. 5,099,846 (Hardy) issued Mar. 31, 1992 relates to combining images from different imaging modalities and is primarily about the software for combining the images such as X-ray and NMR.

U.S. Pat. No. 6,754,519 (Hefetz) issued Jun. 22, 2004 to Elgems discloses two imaging systems such as CT and MRI where the two systems are mounted on a common rail system for rolling movement from a common position to a spaced position.

U.S. Pat. No. 5,291,890 (Cline) issued Mar. 8, 1994 to GE discloses a patient heat treatment system where the heat is detected using an MRI.

U.S. Pat. No. 6,961,606 (DeSilits) issued Nov. 1, 2005 to Phillips discloses two imaging systems such as CT and PET where the two systems are mounted on a common rail system for rolling movement from a common position together for common scanning of the patient to a spaced apart position.

German patent application 39 31 854 of Muller published Apr. 4, 1991 discloses an NMR apparatus using a laser coagulation stereotactic system.

Japanese application 05344964 of Toshiba shows a combination of an X-ray system and an MRI system. This is application is filed only in Japan and provides what is apparently a crude system.

Japanese patent application 4183446 published Jun. 30, 1992 by Res Dev Corp of Japan discloses the use of MRI and X-Ray in a common apparatus.

One element which must be designed for use with a combined imaging system of the type described above is that of the patient support table and components for providing support which are used during the procedures in the MR and X-ray imaging.

Typically during imaging and non-surgical intervention, the patient is merely resting on a suitable support surface which can be just the table or a table with extensions for holding the head or other extremities.

However during surgical procedures it is necessary in many cases to provide structural support components which hold a body part such as the head of the patient stationary during the imaging and during the procedures which follow the imaging.

Such structural support components when used in X-ray imaging systems are typically formed from a material commonly known as Novotex which is supplied by Pro-Med Instruments Inc, Manufacturing and Distribution of Surgical Products and is formed of a phenolic resin reinforced by cotton fibers. This is selected because it has a low absorption factor for X-rays which is measured as an Aluminum equivalence factor and this is typically of the order of 4 mm for 10 mm of material. Usually devices require much thicker material, as much as 25 to 30 mm which takes the Aluminum equivalence factor to 8 to 10 mm.

Such materials including particularly the Novotex material are considered to be MR compatible in that they are non-ferromagnetic so that they can be placed in the magnetic field and they are non-electrically conductive so that they do not affect the radio frequency fields. Novotex also provides the necessary adequate physical characteristics including strength and hardness so that it is to be expected that Novotex can be used for constructions to be used in both MR and X-ray imaging.

In PCT application WO 2010/111772 published Oct. 7, 2010 by the present assignees is disclosed a head clamp for use in a combined MR and X-ray imaging system of the type described above. However up to now it has not been possible with a head clamp to meet the requirements of radio-lucence required by FDA where the attenuation of the device when present in the X-ray image must be less than a factor of 2.3 mm of aluminum equivalent, that is the attention must be less than that of 2.3 mm of aluminum.

All publications, patents, and patent applications mentioned in this specification are herein incorporated by reference to the same extent as if each individual publication, patent, or patent application was specifically and individually indicated to be incorporated by reference.

SUMMARY OF THE INVENTION

It is one object of the present invention to provide head clamp which can be used in a combined MR and X-ray imaging system of the type described above.

According to a first aspect of the invention there is provided a head fixation device for use in imaging of a part of a patient using Magnetic Resonance and X-ray imaging, the device comprising:

first and second skull engaging clamp members arranged so as to engage the skull from opposite sides so as to locate the skull therebetween;

a generally C-shaped support including a base and two legs arranged so that the clamp members are attached to first and second ends of the legs of the C-shaped support the base of the C-shaped support extends around the head from the first leg to the second leg;

and an adjustment system for moving at least one of the clamp members inwardly relative to the other so as to apply a clamping force to the skull;

the adjustment system including a course adjustment system allowing course movement of one leg relative to the other to a position in which the clamp members are brought into engagement with the skull and a fine adjustment system allowing fine movement of said one leg relative to said other leg from said position to apply an adjustable pressure though the clamp members to the skull;

the adjustment system including the course adjustment system and the fine adjustment system being located in the base.

Preferably the adjustment system is located at the base to the side of the C-shaped support thus keeping the adjustment system out of the field of images through the clamped skull taken from the top or bottom as well as from the side.

Preferably the adjustment system comprises a mechanism that located at the bottom of one leg at the base of the C-shaped support.

Preferably the adjustment system provides no adjustment at the connection between the head clamp members and the ends of the legs of the C-shaped support Preferably the force that is applied through the head clamp members is measured using a gauge that measures the force applied by the adjustment system to said one leg.

Preferably the base is fixedly attached to a first one of the legs and the second leg has a slide element mounting in the base for sliding movement along the base to reduce a spacing between the legs.

Preferably the adjustment system includes a hand operated adjustment component mounted in the base at the bottom of the first leg, a screw rotated by the hand operated adjustment component and extending along the base to the second leg and a nut component attached to the slide element of the second leg to drive the slide element along the base.

Preferably the nut component includes a ratchet arrangement which allows the nut component to ratchet along the screw during the course movement.

Preferably the base and the first leg are separable from the slide element and the second leg and is separable from the hand operated adjustment component and from the screw for independent cleaning.

Preferably the hand operated adjustment component includes a latch to hold it in position in the base.

Preferably the screw is arranged to be snap fastened into the hand operated adjustment component and to be released therefrom only on manual action of a release latch.

Preferably the hand operated adjustment component is freely rotatable in a direction to increase the pressure on the skull and is rotatable in an opposite direction to decrease the pressure only on manual action of a release latch.

Preferably longitudinal force on the screw from the nut component caused by pressure on the skull causes compression of a spring and wherein deflection of the spring is indicated to the user by a visual marker element which moves relative to a gauge on the hand operated adjustment component.

Preferably the spring is cylindrical body surrounding the axis of the screw and defining a stack of axially compressible disk springs formed of a polymer material so as to be MR compatible.

Preferably the hand operated adjustment component includes a hand wheel with gauge windows at angularly spaced positions therearound and wherein pressure on the skull causes movement of a visual marker element relative to the gauge windows to indicate the pressure to the user.

Preferably the visual marker comprises a disk movable axially of the hand operated adjustment component with the disk having edges thereof visible in each of the gauge windows.

According to a second aspect of the invention there is provided a head fixation device for use in imaging of a part of a patient using Magnetic Resonance and X-ray imaging, the device comprising:

first and second skull engaging clamp members arranged so as to engage the skull from opposite sides so as to locate the skull therebetween;

a generally C-shaped support including a base and two legs arranged so that the clamp members are attached to first and second ends of the legs of the C-shaped support the base of the C-shaped support extends around the head from the first leg to the second leg;

and an adjustment system for moving at least one of the clamp members inwardly relative to the other so as to apply a clamping force to the skull;

wherein the adjustment system includes a hand operated adjustment component mounted in the base at the bottom of the first leg, a screw rotated by the hand operated adjustment component and extending along the base to the second leg and a nut component attached to the slide element of the second leg to drive the slide element along the base;

and wherein the nut component includes a ratchet arrangement which allows the nut component to ratchet along the screw during the course movement.

According to a third aspect of the invention there is provided a head fixation device for use in imaging of a part of a patient using Magnetic Resonance and X-ray imaging, the device comprising:

first and second skull engaging clamp members arranged so as to engage the skull from opposite sides so as to locate the skull therebetween;

a generally C-shaped support including a base and two legs arranged so that the clamp members are attached to first and second ends of the legs of the C-shaped support the base of the C-shaped support extends around the head from the first leg to the second leg;

and an adjustment system for moving at least one of the clamp members inwardly relative to the other so as to apply a clamping force to the skull;

wherein the adjustment system is arranged such that pressure on the skull causes compression of a spring;

wherein the spring is cylindrical body defining a stack of axially compressible disk springs formed of a polymer material so as to be MR compatible.

According to a fourth aspect of the invention there is provided a head fixation device for use in imaging of a part of a patient using Magnetic Resonance and X-ray imaging, the device comprising:

first and second skull engaging clamp members arranged so as to engage the skull from opposite sides so as to locate the skull therebetween;

a generally C-shaped support including a base and two legs arranged so that the clamp members are attached to first and second ends of the legs of the C-shaped support the base of the C-shaped support extends around the head from the first leg to the second leg;

and an adjustment system for moving at least one of the clamp members inwardly relative to the other so as to apply a clamping force to the skull;

wherein the adjustment system includes a hand operated adjustment component which includes a hand wheel with gauge windows at angularly spaced positions therearound;

and wherein pressure on the skull causes movement of a visual marker element relative to the gauge windows to indicate the pressure to the user.

The head fixation device thus includes independently hand driven mechanisms for application of pressure to support the head; one for coarse adjustment and one for fine adjustment. The coarse adjustment mechanism in the form of a ratcheting plunger, positions the clamp arm near to or at the head such that the fine adjustment mechanism, a torque screw, can be tightened to add and mechanically display pressure.

Radiopacity, which is the resistance of a material to x-ray passage, is proportional to the volume and density of material in the imaging region. The prior art designs place the fine pressure application mechanism at the top of the clamp arm, which interferes with lateral imaging of head region due to the material volume of the mechanism. Similarly, the coarse ratcheting mechanism is located near the center of the base of the skull clamp and interferes with vertical imaging of the head.

This arrangement disclosed herein consolidates both adjustment mechanisms into one drive system for the purpose of improving radiolucency and ergonomics of the design. The arrangement disclosed herein removes the fine adjustment mechanism and associated material volume from the top of the Extension Arm and combines it with the coarse ratcheting mechanism located in the base of the skull clamp. The mechanism is packaged in the base corner of the skull clamp, removing it from interfering with vertical x-ray shots. In addition, the coarse ratcheting plunger has been packaged internally into the Extension Arm reducing material volume and complexity of the Fixed Arm.

The hand wheel of the arrangement disclosed herein acts to consolidate and improve upon the functionality of both the coarse adjustment ratchet plunger and torque screw of the predicate designs.

In a system which provides dual modality imaging using Magnetic Resonance Imaging systems and Radiological (involving X-Ray) equipment, the equipment which remaining the field of view during the imaging proves must be compatible with both modalities. In addition the equipment should be radiolucent in that it should have a low attenuation to X-ray. In particular the Head Fixation Device or head clamp must have no influence on the final image, obtained by those systems. In order to get this, the material, which is using in this device, must have neither ferromagnetic component (that might affect the constant filed of the Magnetic Resonance Imaging system) nor other components that have any electrical conductivity (that might affect the RF field of the Magnetic Resonance Imaging system). From radiological point of view, the material should have relatively low number for Aluminum equivalence parameter, only then it is possible to achieve clear X-ray imaging (taken through this material), which has low signal to noise ratio and without increasing X-ray power.

The device should ideally be configured in such a manner that the majority of the mechanical components are located such that their impact on the images of the body's anatomy are minimized.

The radiolucent head fixation device is made primarily from PEEK (Polyetheretherketone). The use of this material will minimize the attenuation of the device in the X-Ray image.

The device is configured such that the majority of the mass of the mechanical components are located in areas where they will not negatively impact the most useful image orientations of the patients head. The individual components of the device are designed in such a manner that the material that is perpendicular to the image is minimized, which as a result will decrease the visibility of the device during imaging. That is the structure is arranged with the major thickness of the components not in line with the main direction of X-ray travel.

The mechanism that applies and measures the pinning force applied to the patient's skull is located at the base of the skull clamp and to the side keeping the mechanism out of the field of images taken from the top or bottom (normal to the table surface) as well as lateral imaging.

BRIEF DESCRIPTION OF THE DRAWINGS

The following

FIG. 1 is an isometric view of an Angiography room showing a patient table, an MRI magnet movable into a position for imaging the patient on the table and an arrangement for moving an X-Ray system.

FIG. 2 is an isometric view of a table for mounting the patient, the base being omitted for convenience of illustration, and showing the a head clamp for the skull of the patient mounted on the table.

FIG. 3 is an isometric view on an enlarged scale of the head clamp of FIG. 2.

DETAILED DESCRIPTION

The following description is taken from the above PCT application and is included for completeness of disclosure herein.

Figure 1:
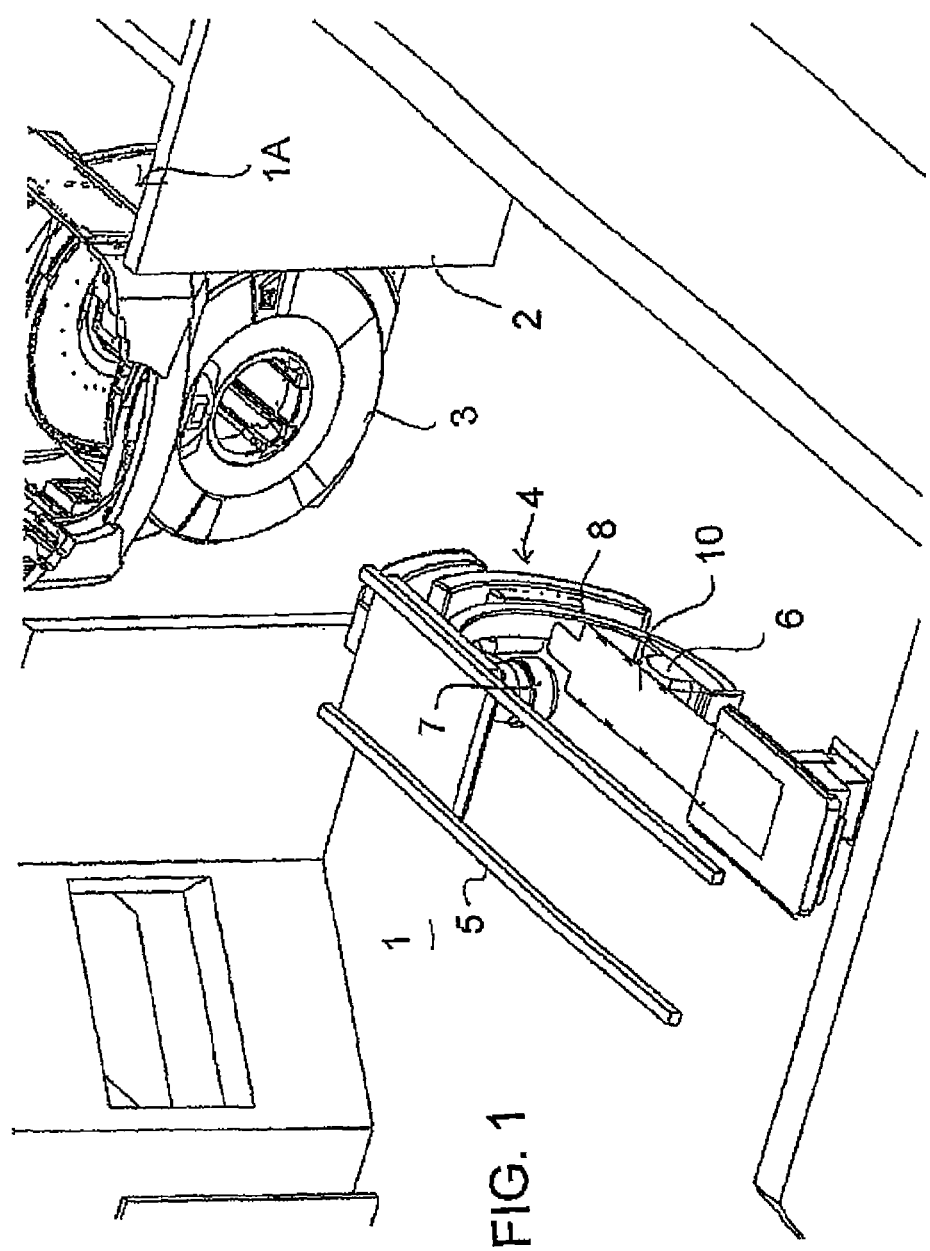
FIGS. 1 to 3 are taken from the above mentioned PCT application WO 2010/111772 published Oct. 7, 2010 and hence are prior art.

In FIG. 1 is shown an arrangement for carrying out Magnetic Resonance Imaging and X-ray imaging of a patient while the patient remains stationary on a patient support table. The arrangement provides a room 1 in which is mounted a patient support table 10 with doors 2 at one side of the room for entry into the room of the magnet 3 of an MR imaging system from a magnet bay 1A. The room contains an X-ray imaging system 4 mounted on rails 5 and includes an X-ray transmitter 6 and receiver 7 mounted on a C-shaped support 8. The X-ray system is of a conventional construction commercially available from a manufacturer such as Siemens. The table 10 described and illustrated herein is used in an arrangement where the patient remains in position on the table while imaging is effected using MRI and X-ray.

Additional unique multi-room layouts, configurations and applications are possible when a rotating MRI system is designed. In this case, the following multi-room configurations are used as examples to illustrate the variety of applications which are possible, with all of these applications being financially beneficial to the healthcare industry.

The magnet system 3 moves into a room within 1 minute, and the doors 2 open within seconds, so the limiting factor on effectiveness of usage of the magnet system is providing the patients into and out of the room, prepping the patients if required, and discussing the imaging with the patients. It is known that a reasonable amount of time per imaging event is 60 minutes, and therefore the movement of the MRI scanner into and out of a room is not the limiting time value. As well, the efficiency of a multi-room system becomes more difficult to schedule as the need for both diagnostic and interventional procedures occurs. The following configurations are now possible:

A three room diagnostic configuration in which the central magnet holding bay 1A houses the magnet and the diagnostic patients are organized in the three rooms including the room 1 and a further room not shown beyond the bay 1A. The doors 2 to room 1 open, the magnet holding bay 1A becomes part of room 1. When the magnet moves to the second room, the magnet may not move but may extend its diagnostic table, the patient lies on the diagnostic table, imaging is performed, no need to do intervention is found, the patient exits the diagnostic table and the magnet moves back into the holding bay, ready for use by one of the other rooms. The magnet then may draw in its table, rotates to the doors for that room, and the process for the other room begins. In this case, the magnet does not move in a translational direction, such as on rails, but simply rotates.

A two room system is in the corner of the hospital. In this case, the magnet both rotates and translates. There is a central magnet holding room, with doors in each of the two 90 degree directions, and the magnet can rotate its diagnostic table in whichever direction is required, or can rotate to allow the opposite end of the magnet to enter the room first. This approach allows existing diagnostic functionality and applications to be used in either room, or allows both rooms to serve as intra-operative rooms without any significant change to magnet controls and monitoring. This two room corner system cannot be done without a rotating magnet.

The system can be suspended from the ceiling or mounted on a floor mounted bearing, with either system providing rotation of the magnet. The MRI system may also be suspended from the ceiling on rails, such that it can also be translated in space using the rail system. The rotational mechanism can either be located between the magnet and the rails, or above the rails. The below track and above track rotators have different properties for different configurations. The below track rotator allows for easiest upgrade of existing sites, whereas the above track rotator works like a roundhouse in a railway yard, in that the rail, MRI system and all associated systems are rotated.

Turning now to the arrangement including the X-ray system which cooperates with the moving magnet described above, the system consists of the movable magnet integrated with an X-ray system such that the patient can be imaged by either modality on the same table. The patient does not move.

The MR is a high-field horizontal or vertical type of magnet system that moves on overhead rails between the two or more rooms as described above. In the system described, one or more of these rooms contains an X-ray system, either a single-plane or a biplane. When the magnet is moved out of the X-ray examination room and a set of RF and X-ray shielded doors is closed, the examination room functions as a conventional X-ray lab and can be used with conventional equipment. In particular, X-ray guided interventions may be performed.

The arrangement may be used in a typical three room configuration with the Angiography Room (AR) on the left, a Diagnostic Room (DR) in the middle, and an Operating Room on the right. The magnet moves on overhead rails between the rooms and can image in each.

When MR imaging is required, the X-ray equipment is safely stowed, the doors open, and the magnet is brought into the room over the patient on the table. The RF shield encompasses the AR so all the equipment in the X-ray examination room is made RF-quiet. MR imaging can then be performed. Afterwards, the magnet is removed from the room, the doors closed, and the X-ray equipment is returned to its working position.

The MR scanner is used to provide information complementary to that obtained using X-ray. It can be used, for example, to perform a baseline assessment prior to intervention as well as to perform a post-intervention assessment. Such an assessment may include perfusion and viability studies of, for example, the heart or of the brain.

As example workflows for the system, consider elective procedures and emergency cases, such as acute stroke or acute coronary syndromes.

In the Elective Procedure Workflow, a preliminary, baseline MR scan can be obtained with the patient either in the diagnostic room or in the angiography room; this is basically a pre-procedure MR scan. The objective is to measure baseline parameters that are clinically relevant. For a cardiac procedure, this may include baseline cardiac function and myocardial viability.

After the MR scan, the patient is transferred to the angiography room if MR imaged in the diagnostic room, or simply remains on the table if already in the Angio room, where coronary or cerebral angiography and angioplasty, followed by stent placement are conducted, if required, in the customary fashion under X-ray fluoroscopy.

The MR Scanner magnet enters the angiography room and acquires the appropriate MR images. After reviewing the MR data and possibly correlating with the X-Ray data, the interventionist can either discharge the patient or continue treatment.

In the emergency Case Workflow, the patient is admitted and undergoes preparation in the Emergency room (both groins shaved, screening for MR examination, metal check, etc.). The patient is brought to AR (in the case of an acute myocardial infarction diagnosed by ECG) and vascular access via the groin is established. MR Imaging could take place in the AR for baseline assessment in order to minimize movement of the acute patient. The scanner is brought into the AR for MR measurement of baseline cardiac function and perfusion imaging in a cardiac case. In the case of stroke, the MR images will reveal if interventional therapy is indicated. In both cases, MR baseline imaging is completed and processed in a minimum time period. In both stroke and cardiac patients angiography and intervention (angioplasty, thrombectomy, or delivery of clot-busting drugs at the site of occlusion) are performed in the customary fashion, under X-Ray fluoroscopy, if so indicated.

The MR Scanner is brought into the AR for subsequent MR images acquisition. After reviewing the MR images and possibly correlation with the X-ray data, the interventionist will discharge the patient or continue with treatment.

In the arrangement for moving the X-ray system as shown in FIG. 1 the MR enters the X-ray examination room and moves over the head end of the table 10. Since the path of the MR passes right through the location of the C-arm stands, the latter must be moved before the magnet may enter. Depending on need, a floor-mounted C-arm stand may be moved on floor rails, floor turntable, or a boom mounted on the floor or wall. Depending on need, a ceiling-mounted C-arm stand may be moved using extended rails to park it at the foot end of the table, by mounting the stand rails on a platform suspended from the movable magnet rails, or by fixing the stand rails on a platform with a telescopic arm to move them laterally.

Using a solution to move a floor-mounted stand together with a mover for a ceiling mounted stand provides a mechanism to move a biplane system. The mover can provide a mounting position of the single plane or biplane at some non-zero angle to the MR rails, e.g., 90 degrees.

The Patient Handling System or support table is shown in FIGS. 2 to 7 as indicated generally at 10. The patient support table includes a base 11 of a conventional construction which allows the base to move a patient support portion 12 to required locations in height and in orientation. Suitable drive mechanisms and couplings are known in the art and thus are not required to be described herein. At the top of the base 12 is mounted the patient support portion in the form of a generally planar body 12 formed of a fiber reinforced plastics material so as to define a surface area sufficient for supporting the patient while lying on the patient support portion. The patient support 12 includes a rear edge 13 at or beyond the feet of the prone patient together with two side edges 14 and 15 spaced by a distance sufficient to receive and contain the legs, body and arms of the patient to be supported by the support portion.

At a forward end 16 is provided a head clamp 20 for mounting and holding the head of the patient.

On top of the patient support portion 12 is provided a mattress 18 which is shaped to overlie the patient support portion 12.

The structural support for the patient is provided by the support portion 12 which is formed of a fiber reinforced resin material where the fibers are laid in sheets and infused by the resin material to provide a flat structural member of sufficient strength to carry the weight of the typical patient. In order that the patient support portion be formed of a material which does not interfere with the operation of the magnet or the generation and acquisition of the necessary signals used in magnetic resonance imaging, the fiber reinforcement selected for use in the structure of the portion 12 is a fiber which has sufficient strength to provide the necessary resistance to bending but a fiber which is non-electrically conductive. Thus carbon fibers cannot be used since long carbon fibers generate or allow currents to flow within the structure of the portion and such currents will interfere with the necessary signals. The currents are generated by the high magnetic fields within the magnet and by the electro magnetic signals which are generated within the magnet for use in the magnetic resonance imaging. Typically aramid fibers such as Kevlar™ can be used in replacement for the carbon fibers typically used in such structures.

The mattress is formed of a stiff foam material encased by a skin to provide an exterior surface which is resistant to fluids and can be readily cleaned for sterilization to be used in clinical situations.

The patient handling system thus contains the following key components: the patient table 11, the head holder 20, and MR imaging coils (not shown). The system, including integration of the key components, is specially designed to permit imaging with both MRI and X-ray imaging modalities, while maintaining sufficient image quality and workflow.

The patient table is designed to allow the patient to be scanned with both MR and X-ray imaging modalities. The patient table is comprised of two major components: the table pedestal and the tabletop. The tabletop is fully MR and X-ray compatible; the table pedestal does not adversely impact image quality during MR scanning (i.e. does not impact homogeneity of magnetic field), the pedestal also does not experience significant forces from the magnetic field. The tabletop is positioned so that the table pedestal (which is also not X-ray compatible) is at a distance that is sufficiently away from the imaging site. The tabletop integrates the head holder, arm boards and MR imaging coils.

The head holder supports the patient's head during the procedure and must also be MR and X-ray compatible. The head holder integrates into the patient table in a manner that is very efficient to position and remove. The MR imaging head coils may also be integrated with the head holder and are easily positioned and removed at the imaging site.

The MR imaging coils consist of head coils for imaging the head and upper spine. MR coils are not X-ray compatible and thus are positioned and removed from the imaging area when switching between imaging modalities without having to move or interfere with the patient.

During certain medical procedures, both X-ray and MR imaging modalities may be employed, at separate times during the procedure. Since MRI coils are generally not X-ray compatible, it is necessary to position and remove the coils quickly and easily when switching between MRI and X-ray imaging. For cases where it is necessary to keep the patient in a fixed position during the procedure, the imaging coils must also be positioned and removed without moving or shifting the patient in any way. For example, cranial procedures will employ the head holder to secure the head of the patient during the entire procedure. The MR imaging head coils will be easily positioned around the head holder without moving the head holder or the patient's head in any way.

The patient table consists of a table top that is completely MR and X-ray compatible. The tabletop also enables the integration of various MR imaging coils, such as head coils and cardiac coils, with the special feature of positioning and removing the coils without moving or shifting the patient in any way.

The tabletop also includes a means of easily positioning and removing the head holder; this includes a ridge or ledge around the head end of the tabletop, where the head holder may slide on with a dovetail interface. The imaging head coils also are integrated to the table in this fashion.

The head holder and table adapter assembly include the head holder that secures the head during the procedure and also a table adapter that secures the head holder to the patient table and also provides a means of adjusting the position/orientation of the head holder. The entire assembly is completely MR and X-ray compatible. There are various means of securing the patient's head, including a horseshoe head holder, a sling/suspender head holder, and a head cradle. The horseshoe head holder includes a rigid frame that is cushioned by gel, foam, or air inflated pillows; the sides and top of the patient's head may be supported by a strap or by side cushions. The frame may also be adjustable for accommodating a large range in head sizes. The sling/suspender head holder consists of soft material (e.g. fabric) that is shaped into a sling to support the back and sides of the head. The top of the head may be supported by a fabric strap; foam padding may insert between layers of material in the sides of the sling to cushion the head where the table adapter interfaces to the sling/suspender head holder. The head cradle is a scoop-shaped device that cradles the head and neck of the patient and includes foam or inflatable air pillows to cushion the back of the patient's head (for comfort) and also preventing the patient from moving the head from side to side. One additional feature of the inflatable pillow is that the pillow may be deflated to bring the head down slightly so that it is even closer to the portion of MR imaging head coil that is positioned directly underneath the head of the patient, which will increase MR image quality. The table adapter may interface to the head holder at various orientations, such as at the front of the head holder (closest to the patient's head), at the back of the head holder (furthest from patient table), along the sides of the head holder, or along the top of the head holder.

Figure 2:
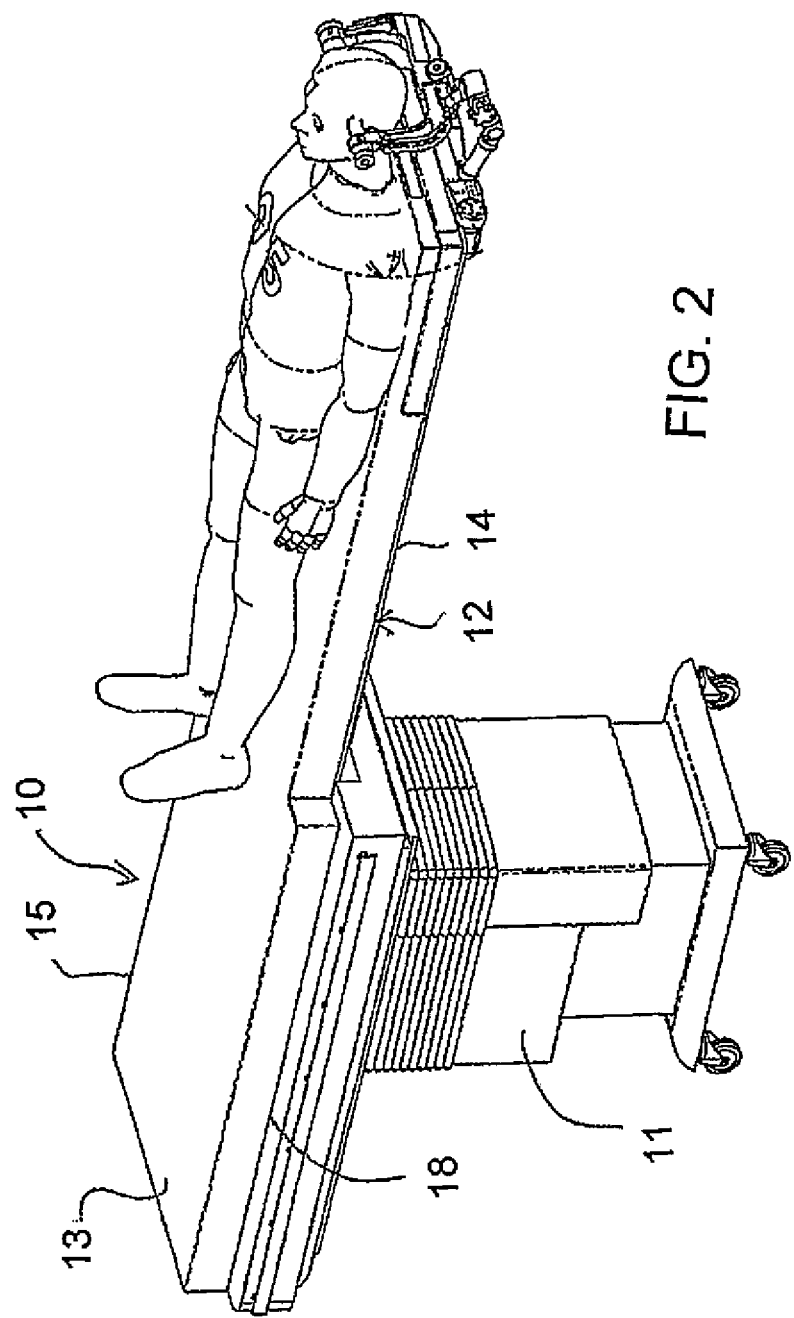
Figure 3:
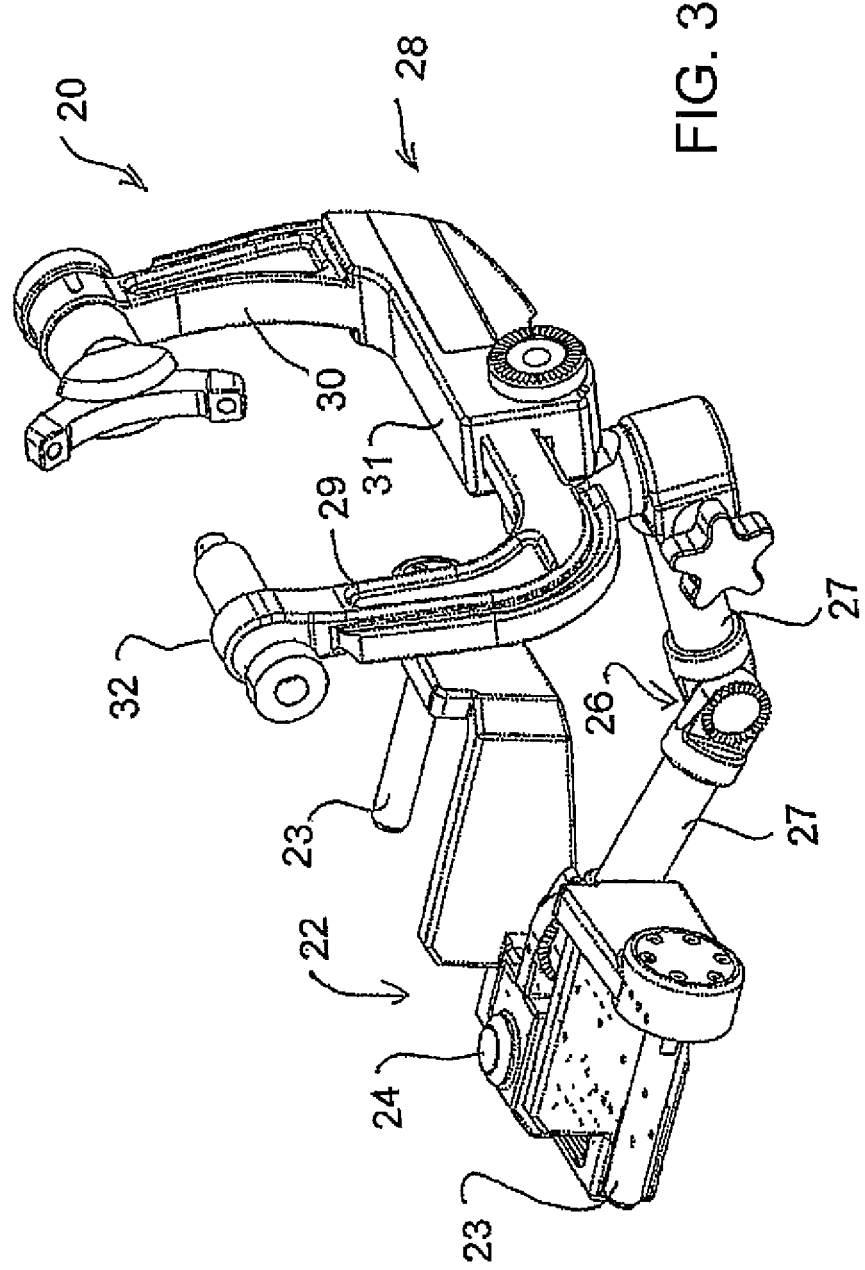

The head holder shown in FIGS. 2 and 3 is described in more detail hereinafter and includes a mounting portion 22 which is connected to the end face of the table 20 by two mounting pins 23. The mounting portion includes a central boss 24 which connects to and supports a link 25 formed by two arms 27 and a plurality of swivel connecting joints 26 which allow the head holder clamp 28 to be moved to different positions to mount the head at a required position. The clamp 28 includes a three point mounting carried on two arms 29 and 30 which can be adjusted in spacing by a rack 31. One of the mounting points is carried on a screw 32 to allow the clamp to engage the head as required.

Turning now to the present invention shown in FIGS. 4 to 9, there is shown head fixation device 50 for use in imaging of a part of a patient, particularly the head, using Magnetic Resonance and X-ray imaging as previously explained.

The device comprises first and second skull engaging clamp members 55, 56 arranged with pins 55A and 56A in suitable orientations so as to engage the skull from opposite sides so as to locate the skull therebetween. The clamp members 55, 56 are carried on a generally C-shaped support 54 including a base 52 and two legs 51, 53 upstanding from the base 52. Thus the clamp members 55, 56 are attached to upper ends of the first and second legs 51, 53 of the C-shaped support 54 with the base 52 of the C-shaped support extends around or across the head from the first leg to the second leg.

An adjustment system 57 is provided for providing relative movement of the clamp members 55, 56 inwardly and outwardly relative so as to apply a clamping force to the skull. The clamping device 50 is carried on an adjustable frame (not shown in these Figures) as previously described so as to hold the device underneath the head and thus to support the head in an adjusted fixed position relative to the table.

The C-shaped support member 54 comprises a C-shaped or generally arch shaped inner band 61 adjacent the skull, an outer band 62 generally following the shape of inner band but spaced outwardly from the inner band and a plurality of spaced bars 63 extending between the inner band 61 and the outer band 62 in the form of a truss. Thus the bars 63 extend back and forth in diagonal zig zag manner between the bands as indicated at 63A, 63B and meet at apexes 63C, 63D at the inner and outer bands. Some of the bars cross to form an X-truss construction. The bars 63 are equal in width W in a direction D longitudinal to the bed relative to the width of the bands 61, 62.

The C-shaped support is made primarily from PEEK (Polyetheretherketone). However other suitable materials can be provided which are compatible with MR and X-ray imaging.

Figure 4:
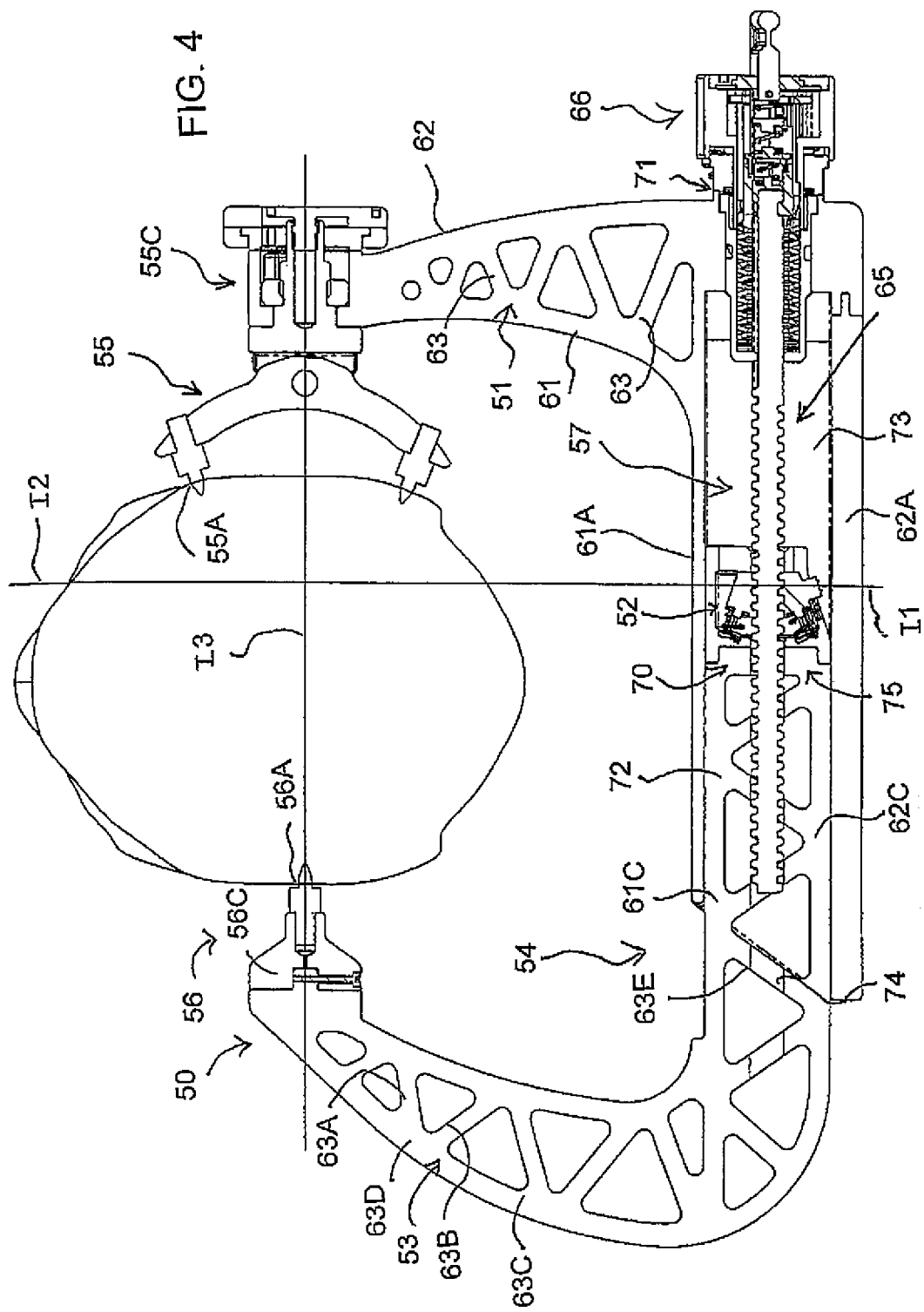
FIG. 4 is a vertical cross-sectional view of the head clamp of the type generally shown FIGS. 2 and 3 showing further details according to the present invention.

This construction of the support with the bands and bars provides a configuration such that the majority of the mass of the mechanical components are located in areas where they will not negatively impact the most useful image orientations of the patients head. That is the material that is perpendicular to the image, that is in the plane of the FIG. 4, is minimized, which as a result will decrease the visibility of the device during imaging. That is there is no conventional web of an I-beam in the support of the type shown for example manufactured by Doro. That is the C-shaped support is arranged with the major thickness of the bands and bars not in line with the main direction of X-ray travel.

The adjustment system 57 comprises a screw mechanism 65 that adjusts by a hand operated adjustment component or hand wheel 66. The screw as it rotates as driven by the hand operated adjustment component 66 changes the width of the C-shaped member at the base 52 of the C-shaped member so as to decrease the distance between the legs 51, 53 of the C-shaped member. The screw 65 is located at the base 52 of the C-shaped support and to the side of the C-shaped support under the leg 51 with the hand wheel 66 outwardly of the leg 51 thus keeping the adjustment system out of the field of images of the skull taken from the top 11 or bottom 12 as well as lateral imaging 13.

As the adjustment occurs at the base, the adjustment system provides no adjustment at the connection 55C and 56C between the head clamp members and the ends of the legs 51 and 52 of the C-shaped support. Thus these connections 55C, 56C can be of a simple low mass construction only allowing it to be detached from the assembly such that another 2-pin rocker arm could be attached.

The adjustment system 57 includes a course adjustment system 70 allowing course movement of one leg relative to the other to a position in which the clamp members are brought into engagement with the skull and a fine adjustment system 71 allowing fine movement of said one leg relative to said other leg from said position to apply an adjustable pressure though the clamp members to the skull.

The base 52 is fixedly attached to the leg 51 and the second leg 53 is attached to a slide element 72 mounted in the base for sliding movement along the base to reduce a spacing between the legs. The base includes a tubular receptacle defined by a portion 61A of the inner band 61, a portion 62A of the outer band 62 and two side walls 73 spaced on either side of the bands to form a generally rectangular cross section into which the slide element 72 can slide. The slide element is an extension of the leg 53 and includes inner band portion 61C and outer band portion 62C and truss members 63E. A bore 74 allows the screw 65 to pass through.

The adjustment system includes the hand operated adjustment component or hand wheel 66 mounted in the base at the bottom of the first leg 51. The hand wheel 66 attaches to the screw 65 which is rotated by the hand operated adjustment component 66 and extends along the base within the base to the second leg 53 and a nut component 75 attached to the slide element 72 of the second leg 53 to drive the slide element 72 along the base 52.

The nut component 75 is formed in two parts which can slide apart to provide a ratchet arrangement 70 which allows the nut component 75 to ratchet along the screw to provide the course movement. That is, with the screw and hand wheel assembled, the slide element 72 is inserted into the opening into the tubular opening in the base and moved along the base until the nut component 75 engages the end of the screw. At this position the nut component flexes apart allowing the threads of the screw to ratchet through the nut component as each thread pushes the nut component apart. This course movement is continued near to the position where the pins 55A, 56A engage the skull.

At this position the course movement is halted and the fine movement is operated by the operator rotating the hand wheel 66 to turn the screw 65. This pulls the nut component axially toward the hand wheel 66 and thus drives the slide element and the leg along the base to increase pressure on the skull up to a required pressure, which varies depending upon various characteristics of the patient and situation.

Because the screw pulls the nut component it applies the force to the nut component in the opposite direction to that applied during the course pushing movement so that the ratchet action no longer operates and the nut component is pulled down tight onto the threads of the screw.

Thus the adjustment system including both the course adjustment system and the fine adjustment system is located in the base and is located at the base to the side of the C-shaped support thus keeping the adjustment system and particularly the complex hand wheel arrangement described in more detail later out of the field of images through the clamped skull taken from the top or bottom as well as from the side. The screw itself and the nut component are located in the vertical images but do not provide sufficient material to cause unacceptable artifacts in the X-ray imaging.

Figure 5:
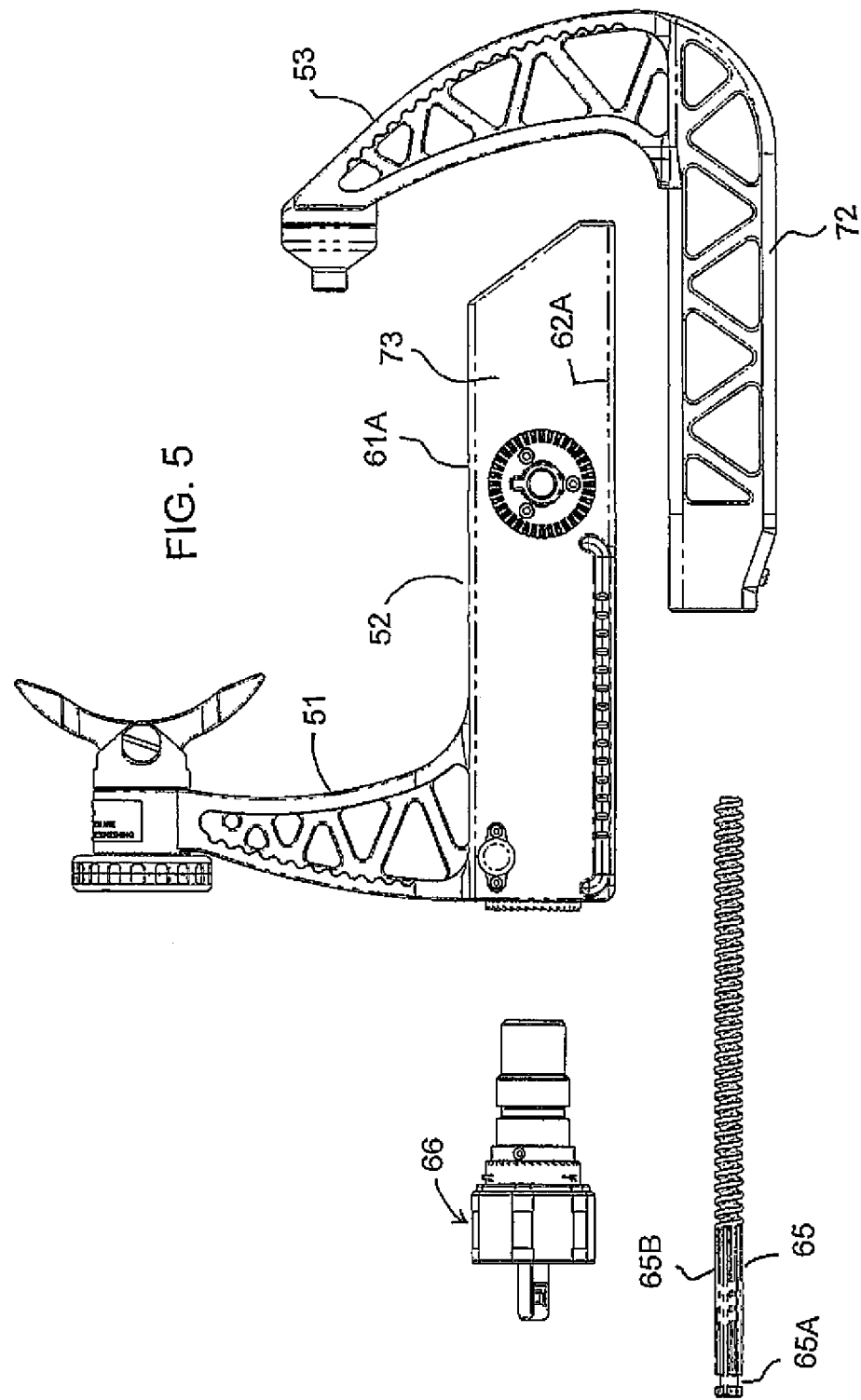
FIG. 5 is a front elevational view of the head clamp of FIG. 4 showing the parts disassembled.
Figure 6:
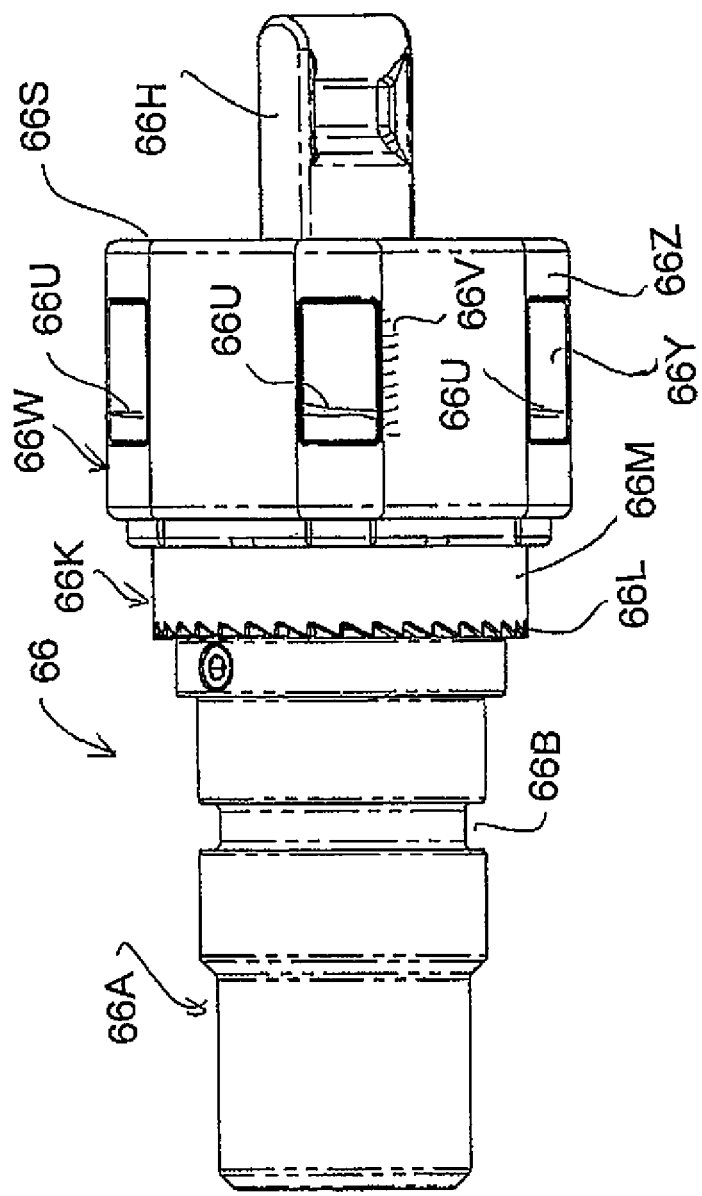
FIG. 6 is a front elevational view of the hand operated adjustment component of the head clamp of FIG. 4.
Figure 7:
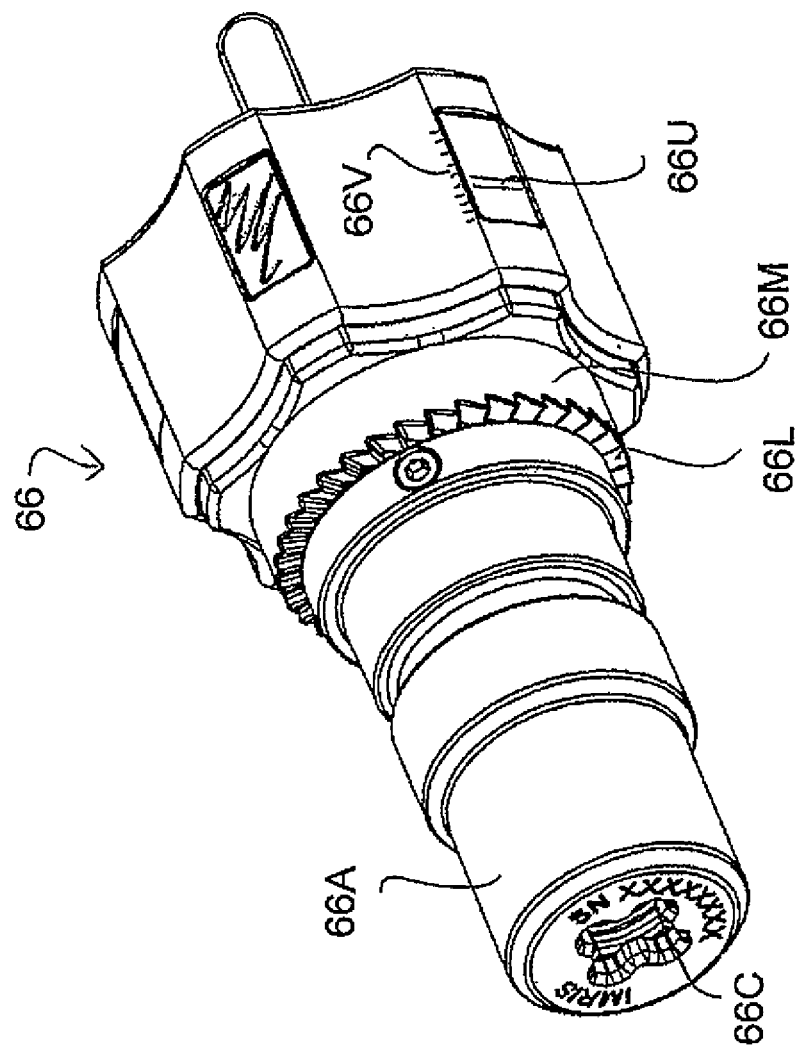
FIG. 7 is an isometric view of the hand operated adjustment component of the head clamp of FIG. 4.
Figure 8:
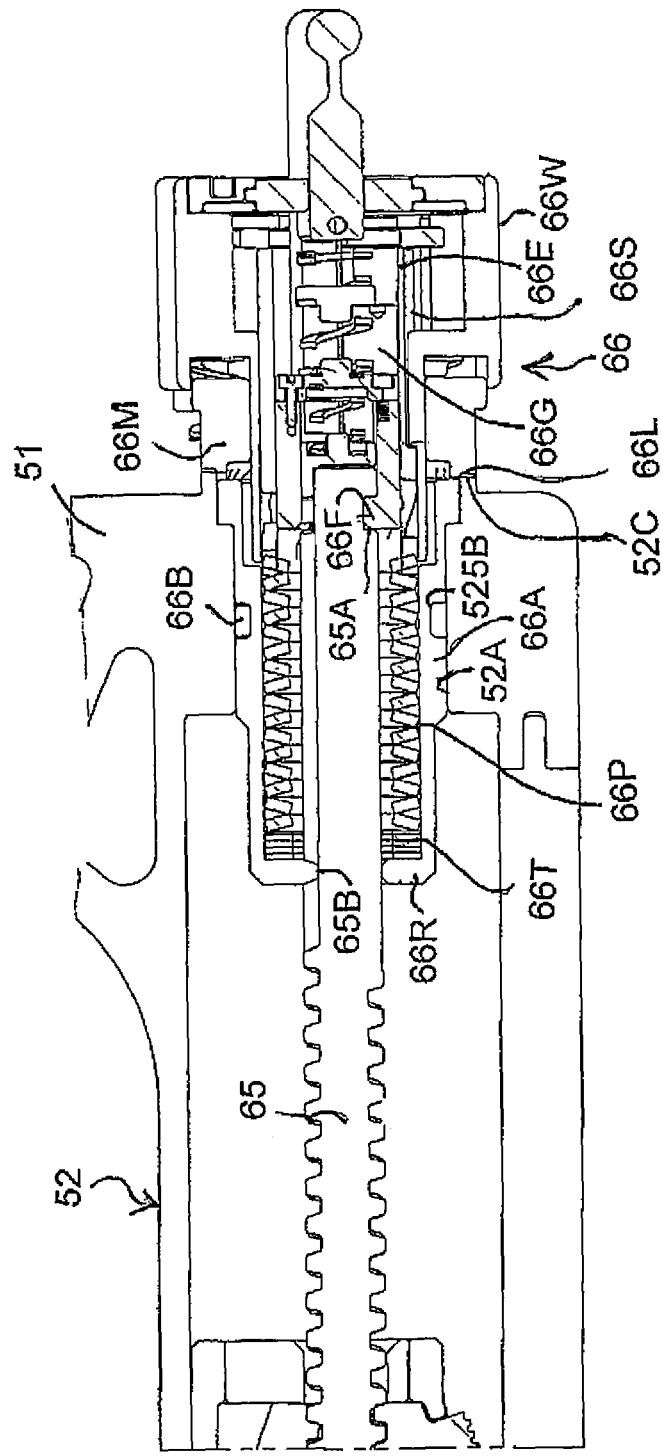
FIG. 8 is a part of the vertical cross sectional view taken from FIG. 4 on an enlarged scale.
Figure 9:
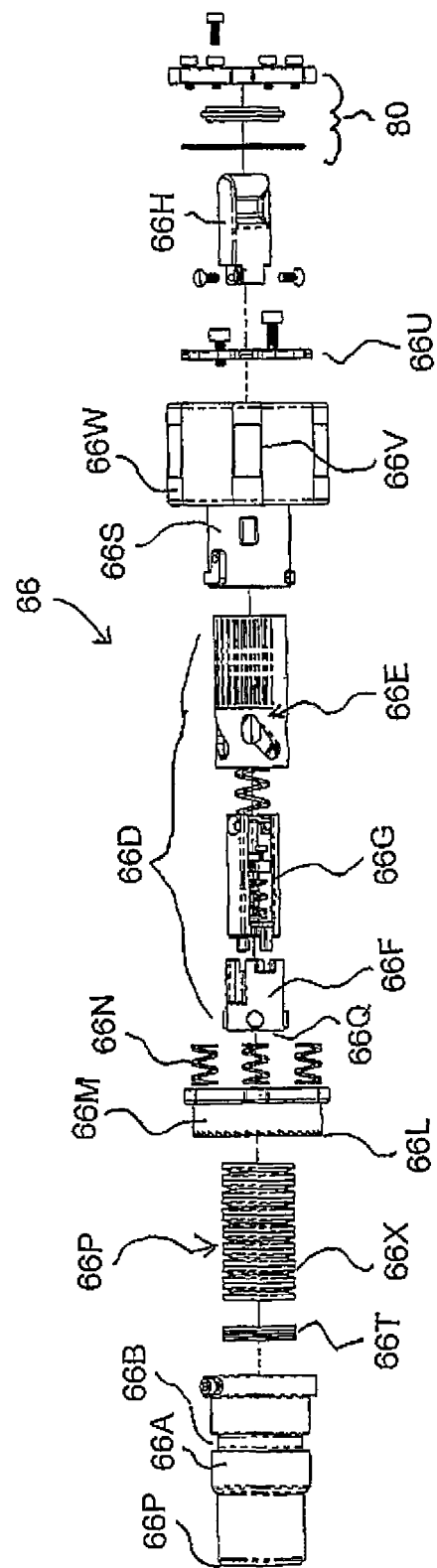
FIG. 9 is an exploded view of the components of the hand operated adjustment component of the head clamp of FIG. 4.

As shown in FIG. 5, the component defining the base 52 and the first leg 51 is separable from the component defining the slide element 72 and the second leg 53 and is separable from the hand operated adjustment component 66 and from the screw 65 for independent cleaning.

The component 66 includes a manually graspable hand wheel portion 66W and a stub portion 66S extending forwardly therefrom into the base 52.

The component 66 has a cylindrical insert portion 66A surrounding the stub portion 66S which slides into a recess 52A in the end wall of the base 52 at the leg 51. The cylindrical insert 66A includes an annular recess around its periphery which receives a latch 52B of the base to hold the component 66 in position in the base at a required angular position. The component 66 is thus held in position until actively released from the base by an operation of the latch for disconnection and separate cleaning.

The screw includes a non-circular end portion which cooperates with a similarly shaped receptacle 66C in the component 66 so that hand driven rotation of the component 66 also acts to drive the screw for pulling in the nut component and the slide element.

The screw 65 also includes a recess 65A adjacent its end at the component 66 which is arranged to be snap fastened into the latch mechanism traveller assembly, 66D, of the component 66 and to be released therefrom only on manual action of a release latch tab 66H. This includes a hub 66F which connects to the cam traveller 60E and acts to drive the hub in its rotation. Two latch portions 66E and 66G receive the end of the screw beyond the recess 65A and rotate around screw 65 by a portion of ⅛ turn so that 66G can lock the non-circular end in place. The screw 65 enters 66 through grooves in 66A that align 65 for engagement with components 66E and 66G. When locked 65 cannot be retracted because the peripheral shape has been turned to be out of alignment with the opening in the hub 66F. A manually operable release 66H, connected to 66G, at the end face 66J of the hand wheel 66W can be pulled back and rotated when required to release the screw from its engagement by turning it back to the position where it is aligned with the bore in the drive hub 66F and 65 can be pulled back out of the component 66 for separate cleaning.

The component 66 as driven by the wheel 66W is freely rotatable in a direction to drive the screw to increase the pressure on the skull. This rotation drives the screw around its axis while the screw is held against unrestrained movement by engagement of the component 66 into the base. The screw thus acts to pull on the nut component 75 to pull the clamp into tension on the head of the patient. The rotation of the screw in the opposite direction to decrease the pressure is only possible on manual action of a release latch. The latch is provided by a one way ratchet 66K including an annular set of ratchet teeth 66L carried on a collar 66M. The teeth cooperate with a set of teeth 52C on a collar on the base 52 so that the hand wheel can only rotate in one direction as controlled by the intermeshing teeth. The collar 66M can be retracted against springs 66N pressing on the end of the hand wheel 66W by the user pulling rearwardly on the collar 66M which releases the meshing action between the teeth allowing the hand wheel to be rotated in the pressure release direction. The latch thus prevents unintentional pressure release which could cause a catastrophic release of the head from the clamp.

The force that is applied through the head clamp members is measured using a gauge that measures the force applied by the adjustment system. Thus longitudinal force on the screw 65 from the nut component caused by pressure on the skull causes compression of a spring 66P which is compressed between the component 66E, as 66F has been rotated up and clockwise to engage 65. A shim 66T is located between the end face 66R and the end of the spring 66P for adjustment. Deflection of the spring caused by the pressure on the hub from the pulling action on the screw is indicated to the user by a visual marker element 66U which moves relative to a gauge 66V on the hand operated adjustment component.

The spring 66P is cylindrical body surrounding the axis of the screw and defining a stack of axially compressible disk springs 66X formed of a polymer material so as to be MR compatible.

The hand wheel has valleys and ribs at spaced positions around the hand wheel and each rib 66Z has a respective one of a series of gauge windows 66Y so that the windows 66Y are arranged at angularly spaced positions around the hand wheel 66W. Thus pressure on the skull causes proportional movement of a disk forming the visual marker element relative to the gauge windows 66Y to indicate the pressure by the gauge 66V to the user. The disk 66U is attached to the end of the components 66E so that it moves forwardly toward the end wall 66R as the spring 66P collapses under the pressure. The disk has a peripheral edge visible in each of the gauge windows so that whatever orientation of the hand wheel takes up, the user can see a respective one of the windows and can see the position of the visual edge in the window at the gauge.

The three primary mechanisms built into this device include the following:

Twist-Lock Carriage Mechanism: To attach the Threaded Drive Rod 65 to the Drive Knob 66, the user pushes the threaded drive rod previously inserted through the splined recess of the drive knob Housing Base 66R and 66F against a spring loaded Top Lock component 66G of the Twist-Lock Carriage 66G that will rise and twist the Twist-Lock Carriage Base 66G along the helical channel of the Item 66E Linear Travel Carriage. The Twist Lock Carriage 66G will slide along the splined heads of the Threaded Drive Rod and after the carriage has travelled approximately 45 deg the Top Lock will slide off the top of Threaded Drive Rod heads and into the pockets next to each head providing a mechanical stop that prevents the Threaded Drive Rod from returning down the helical track. A Quick Release Tab 66H is paired with this locking carriage to raise the carriage Top Lock and release the Threaded Drive Rod with a ⅛th counter-clockwise turn. Two springs actuate this mechanism, one controlling the location of the Top Lock 66G of the carriage and one controlling the location of the Twist-Lock Carriage along the splines of the Linear Travel Carriage.

Force Gauge Mechanism: A splined interface Linear Travel Carriage 66F is preloaded against a series of Disc Springs 66P bound by the Housing Base 66R and Housing 66S. The Disc Springs 66X are designed to produce quasi-linear spring performance and permit application force of the clamp arms to be visually tracked along the six Force Gauge Windows 66Y of hand wheel 66W through the attached Force Traveller Disc 66U. The six windows are provided for easy viewing of the application force. The Linear Travel Carriage 66E travels along splines in the Housing 66S and provides a positive stop that when pre-loaded with against housing 66S mechanically locates the splined carriage 66E and force traveller 66U to the zero force line on the Force Gauge Windows 66Y of the Housing 66. The spring constant can be modified to a limited extent through addition or removal of a series of polymer shims 66T that will modify the pre-load.

Fine Adjustment Lock: A fine adjustment Locking Disc 66M provides a positive lock to the drive system that will prevent accidental pressure release during use. The drive knob can be used to apply any pressure required by the operator up to 80 lb (360 N) and will lock the device in increments of 1 lb (4 N). The Force Gauge Windows 66Y present scale increment lines of 10 lb and 20 lb. The plunger lock 66M is driven by three springs 66N and is bound between a shoulder of the Housing Base and Housing when separated from the base 52. When installed in the base 52 the plunger lock runs on an inverse tooth profile provided on the collar 52C. The Drive Knob Plunger Lock keeps the Drive Knob 66 contained in the base 52 as the Extension Arm or slide element 72 is being pulled into location by hand.

Note torque is transferred to the threaded drive rod primarily through the splined connection 66E. The upper discs 80 of the design provide a lid for the top of the drive knob 66 and indicate to the user if the drive knob is locked or unlocked to the threaded rod.

In addition to the reduction in radiopacity described in the sections above, a key benefit for quality of X-ray imaging, an ergonomic benefit exists because there is only one mechanism requiring inspection for locking and pressure indication. Secondary benefits of the design exist from the packaging of device mechanisms into one location and include improved cleanability of the base 52 and manufacturability of the device.

In addition to the mechanics of the Drive Knob 66, the location of the consolidated system in the bottom corner of the Fixed Arm away from the two of the primary imaging orientations (vertical and lateral) provides the advantages described above.

The invention claimed is:

1. A head fixation device for use in imaging of a part of a patient using Magnetic Resonance and X-ray imaging, the device comprising:
   first and second skull engaging clamp members arranged so as to engage the skull from opposite sides so as to locate the skull therebetween;
   a generally C-shaped support including a base and two legs arranged so that the clamp members are attached to first and second ends of the legs of the C-shaped support the base of the C-shaped support extends around the head from the first leg to the second leg;
   and an adjustment system for moving at least one of the clamp members inwardly relative to the other so as to apply a clamping force to the skull;
   the adjustment system including a course adjustment system allowing course movement of one leg relative to the other to a position in which the clamp members are brought into engagement with the skull and a fine adjustment system allowing fine movement of said one leg relative to said other leg from said position to apply an adjustable pressure though the clamp members to the skull;
   the adjustment system including the course adjustment system and the fine adjustment system being located in the base.

2. The device according to claim 1 wherein the adjustment system is located at the base to the side of the C-shaped support thus keeping the adjustment system out of the field of images through the clamped skull taken from the top or bottom as well as from the side.

3. The device according to claim 1 wherein the adjustment system comprises a mechanism that located at the bottom of one leg at the base of the C-shaped support.

4. The device according to claim 1 wherein the adjustment system provides no adjustment at the connection between the head clamp members and the ends of the legs of the C-shaped support.

5. The device according to claim 1 wherein the force that is applied through the head clamp members is measured using a gauge that measures the force applied by the adjustment system to said one leg.

6. The device according to claim 1 wherein the base is fixedly attached to a first one of the legs and the second leg has a slide element mounting in the base for sliding movement along the base to reduce a spacing between the legs.

7. The device according to claim 6 wherein the adjustment system includes a hand operated adjustment component mounted in the base at the bottom of the first leg, a screw rotated by the hand operated adjustment component and extending along the base to the second leg and a nut component attached to the slide element of the second leg to drive the slide element along the base.

8. The device according to claim 7 wherein the nut component includes a ratchet arrangement which allows the nut component to ratchet along the screw during the course movement.

9. The device according to claim 6 wherein the base and the first leg is separable from the slide element and the second leg and is separable from the hand operated adjustment component and from the screw for independent cleaning.

10. The device according to claim 9 wherein the hand operated adjustment component includes a latch to hold it in position in the base.

11. The device according to claim 9 wherein the screw is arranged to be snap fastened into the hand operated adjustment component and to be released therefrom only on manual action of a release latch.

12. The device according to claim 1 wherein the hand operated adjustment component is freely rotatable in a direction to increase the pressure on the skull and is rotatable in an opposite direction to decrease the pressure only on manual action of a release latch.

13. The device according to claim 1 wherein longitudinal force on the screw from the nut component caused by pressure on the skull causes compression of a spring and wherein deflection of the spring is indicated to the user by a visual marker element which moves relative to a gauge on the hand operated adjustment component.

14. The device according to claim 13 wherein the spring is cylindrical body surrounding the axis of the screw and defining a stack of axially compressible disk springs formed of a polymer material so as to be MR compatible.

15. The device according to claim 1 wherein the hand operated adjustment component includes a hand wheel with gauge windows at angularly spaced positions therearound and wherein pressure on the skull causes movement of a visual marker element relative to the gauge windows to indicate the pressure to the user.

16. The device according to claim 15 wherein the visual marker comprises a disk movable axially of the hand operated adjustment component with the disk having edges thereof visible in each of the gauge windows.

17. A head fixation device for use in imaging of a part of a patient using Magnetic Resonance and X-ray imaging, the device comprising:
    first and second skull engaging clamp members arranged so as to engage the skull from opposite sides so as to locate the skull therebetween;
    a generally C-shaped support including a base and two legs arranged so that the clamp members are attached to first and second ends of the legs of the C-shaped support the base of the C-shaped support extends around the head from the first leg to the second leg;
    and an adjustment system for moving at least one of the clamp members inwardly relative to the other so as to apply a clamping force to the skull;
    wherein the adjustment system includes a hand operated adjustment component mounted in the base at the bottom of the first leg, a screw rotated by the hand operated adjustment component and extending along the base to the second leg and a nut component attached to the slide element of the second leg to drive the slide element along the base;
    and wherein the nut component includes a ratchet arrangement which allows the nut component to ratchet along the screw during the course movement.

18. A head fixation device for use in imaging of a part of a patient using Magnetic Resonance and X-ray imaging, the device comprising:
    first and second skull engaging clamp members arranged so as to engage the skull from opposite sides so as to locate the skull therebetween;
    a generally C-shaped support including a base and two legs arranged so that the clamp members are attached to first and second ends of the legs of the C-shaped support the base of the C-shaped support extends around the head from the first leg to the second leg;
    and an adjustment system for moving at least one of the clamp members inwardly relative to the other so as to apply a clamping force to the skull;
    wherein the adjustment system is arranged such that pressure on the skull causes compression of a spring;
    wherein the spring is cylindrical body defining a stack of axially compressible disk springs formed of a polymer material so as to be MR compatible.

19. A head fixation device for use in imaging of a part of a patient using Magnetic Resonance and X-ray imaging, the device comprising:
    first and second skull engaging clamp members arranged so as to engage the skull from opposite sides so as to locate the skull therebetween;
    a generally C-shaped support including a base and two legs arranged so that the clamp members are attached to first and second ends of the legs of the C-shaped support the base of the C-shaped support extends around the head from the first leg to the second leg;
    and an adjustment system for moving at least one of the clamp members inwardly relative to the other so as to apply a clamping force to the skull;
    wherein the adjustment system includes a hand operated adjustment component which includes a hand wheel with gauge windows at angularly spaced positions therearound;
    and wherein pressure on the skull causes movement of a visual marker element relative to the gauge windows to indicate the pressure to the user.

* * * * *